US010105480B2

(12) United States Patent  
Kopperschmidt

(10) Patent No.: US 10,105,480 B2  
(45) Date of Patent: Oct. 23, 2018

(54) CONTROL UNIT AND METHOD FOR DETERMINING THE PRESSURE IN A BLOOD VESSEL, IN PARTICULAR IN AN ARTERIOVENOUS FISTULA

(71) Applicant: Fresenius Medical Care Deutschland GmbH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 354 days.

(21) Appl. No.: 14/786,687

(22) PCT Filed: Apr. 17, 2014

(86) PCT No.: PCT/EP2014/057952  
§ 371 (c)(1),  
(2) Date: Oct. 23, 2015

(87) PCT Pub. No.: WO2014/173828  
PCT Pub. Date: Oct. 30, 2014

(65) Prior Publication Data  
US 2016/0074571 A1    Mar. 17, 2016

(30) Foreign Application Priority Data  
Apr. 24, 2013 (DE) .................. 10 2013 007 044

(51) Int. Cl.  
*A61M 1/36* (2006.01)  
*A61M 1/14* (2006.01)  
(Continued)

(52) U.S. Cl.  
CPC ....... *A61M 1/3656* (2014.02); *A61B 5/02158* (2013.01); *A61B 5/6866* (2013.01);  
(Continued)

(58) Field of Classification Search  
CPC ............ A61B 5/02152; A61B 5/02158; A61B 5/6866; A61B 5/021; A61B 5/02141;  
(Continued)

(56) References Cited

U.S. PATENT DOCUMENTS 4,342,218 A * 8/1982 Fox .................. G01L 27/005  
                                                              600/486  
5,382,227 A * 1/1995 Riquier ............... A61M 1/3627  
                                                             128/DIG. 13  
(Continued)

FOREIGN PATENT DOCUMENTS

DE           4024434           2/1992  
DE         19917197           7/2000  
(Continued)

*Primary Examiner* — Adam Marcetich  
(74) *Attorney, Agent, or Firm* — Jacobson Holman, PLLC.

(57) ABSTRACT

The invention relates to a control unit (30) for determining the pressure in a blood vessel (A, V, F), in particular in an arteriovenous fistula (F), which is in fluid connection with at least one section (28, 41) of a blood line system (39), in particular an extracorporeal blood circulation (II), at least one pressure-generating device (3, 8, 19, 24, 26) being assigned to the blood line system (39), this pressure-generating device being suitable for acting on the section (28, 41), and the control unit (30) being configured to perform the following steps:

a) being sure that none of the at least one pressure-generating device (3, 8, 19, 24, 26) acts on the section (28, 41),  
b) interrupting the fluid connection of the section (28, 41) with the blood vessel (A, V, F) by triggering an interrupt means (11, 29),  
c) setting the pressure in the section (28, 41) at a predetermined ideal value, in particular at the ambient pressure, with the help of a pressure sensor (13, 14) in the section (28, 41),  
d) restoring the fluid connection of the section (28, 41) with the blood vessel (A, V, F) by triggering the interrupt means (11, 29), and  
e) measuring a resulting pressure in the section (28, 41) with the help of the pressure sensor (13, 14).

20 Claims, 1 Drawing Sheet

(51) Int. Cl.
*A61B 5/00* (2006.01)
*A61B 5/0215* (2006.01)

(52) U.S. Cl.
CPC .. *A61B 5/02152* (2013.01); *A61M 2205/3303* (2013.01); *A61M 2205/3341* (2013.01); *A61M 2205/3344* (2013.01); *A61M 2205/3358* (2013.01); *A61M 2230/04* (2013.01)

(58) Field of Classification Search
CPC ..... A61B 5/0215; A61B 5/02; A61B 5/02007; A61M 1/3656; A61M 2205/3303; A61M 2205/3341; A61M 2205/3344; A61M 2205/3358; A61M 2230/04; A61M 1/3655; A61M 2205/3331; A61M 2205/3327; A61M 1/3639
See application file for complete search history.

(56) References Cited

U.S. PATENT DOCUMENTS

| | | | |
|---|---|---|---|
| 6,623,443 B1* | 9/2003 | Polaschegg | A61M 1/3639 210/646 |
| 2006/0254982 A1* | 11/2006 | Kopperschmidt | A61M 1/342 210/646 |
| 2009/0101577 A1* | 4/2009 | Fulkerson | A61B 5/412 210/646 |
| 2010/0114005 A1* | 5/2010 | Rovatti | A61M 1/16 604/6.15 |
| 2010/0275673 A1* | 11/2010 | Kouda | A61M 1/3639 73/1.57 |
| 2011/0034814 A1* | 2/2011 | Kopperschmidt | A61M 1/3639 600/485 |
| 2011/0230772 A1 | 9/2011 | Koball et al. | |
| 2011/0301472 A1 | 12/2011 | Grober et al. | |
| 2012/0318740 A1* | 12/2012 | Ekdahl | A61M 1/3626 210/646 |
| 2013/0150768 A1* | 6/2013 | Sakamoto | A61M 1/16 604/6.09 |
| 2013/0204542 A1* | 8/2013 | Olde | A61M 1/3653 702/35 |
| 2014/0277894 A1* | 9/2014 | Doyle | G01C 21/3407 701/23 |

FOREIGN PATENT DOCUMENTS

| | | |
|---|---|---|
| DE | 102008059379 | 6/2010 |
| DE | 102008061122 | 6/2010 |
| EP | 2009415 | 12/2008 |

\* cited by examiner

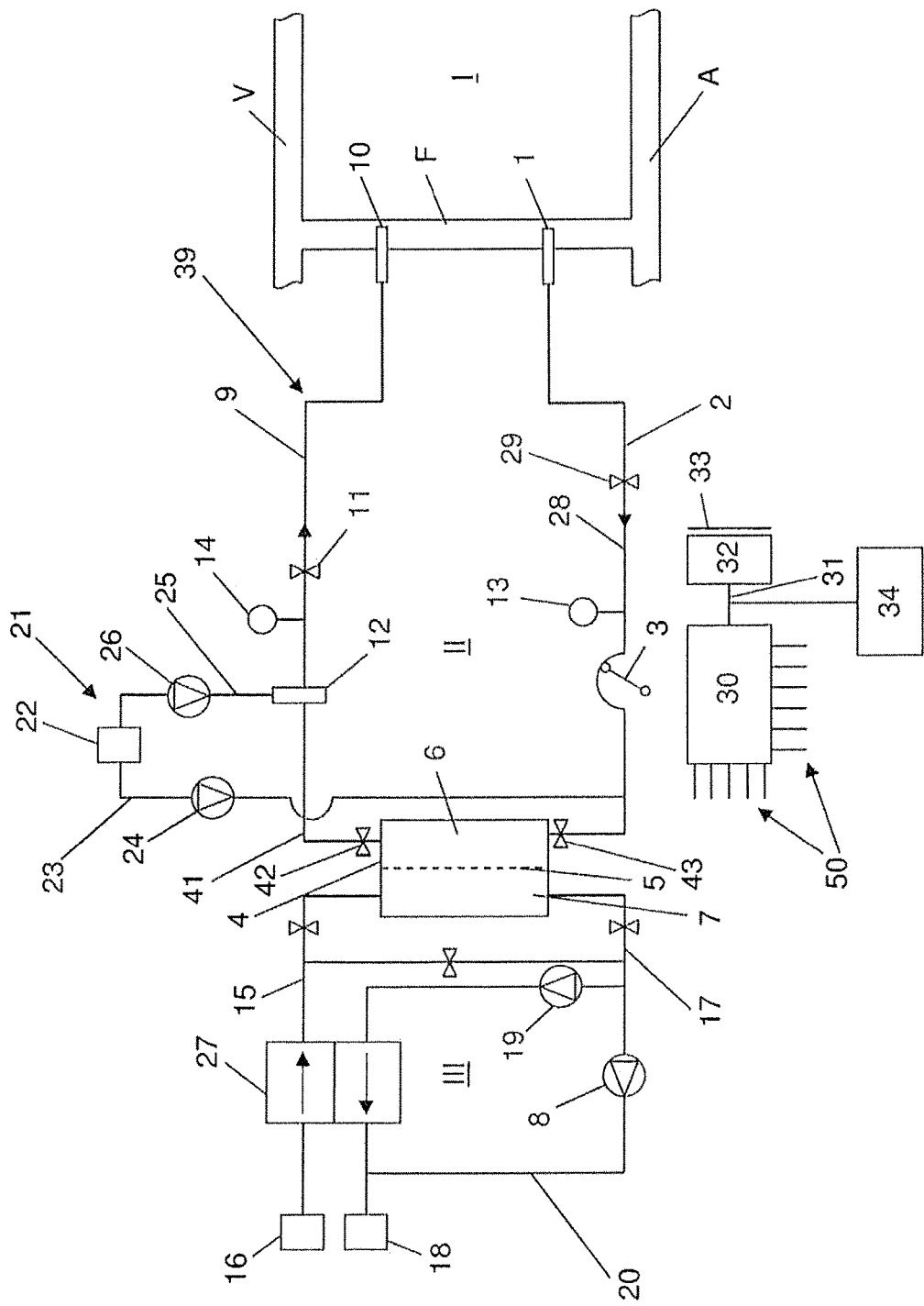

CONTROL UNIT AND METHOD FOR DETERMINING THE PRESSURE IN A BLOOD VESSEL, IN PARTICULAR IN AN ARTERIOVENOUS FISTULA

The present invention relates to a control unit for determining the pressure in a blood vessel, in particular in an arteriovenous fistula, a method for determining the pressure in a blood vessel and a blood treatment machine.

In methods in chronic blood purification therapy, blood is sent through an extracorporeal blood circulation. In hemodialysis (HD), blood is purified by a dialyzer, which has a blood chamber in the extracorporeal blood circulation and a dialysis fluid chamber separated from the former by a semipermeable membrane. Dialysis fluid flows through the dialysis fluid chamber during a hemodialysis treatment, so that certain substances are transported through the membrane by diffusion between the blood and the dialysis fluid and are removed with the dialysis fluid through a dialysis fluid circulation. In hemofiltration (HF), certain substances are filtered out of the blood by a filter membrane based on convection. Hemodiafiltration (HDF) is a combination of these two methods.

Fluid withdrawn from a patient in a blood purification process can be replaced by a substitute fluid, which is added to the extracorporeal blood circulation during the blood treatment.

Tubing systems, which are inserted into the blood treatment machine, such as an HDF machine, are used in blood treatment.

Extracorporeal blood treatment machines contain several pumps which transport the patient's blood and the substituate fluid in the tubing lines of the tubing systems. Mainly peristaltic pumps are used, so that at least one constriction or occlusion moves along the elastic tubing which functions as the pump space. In the most conventional design of peristaltic hose pumps, the elastic tubing is completely closed off at the constriction or occlusion. These pumps are therefore also referred to as occluding hose pumps. The most conventional type of occluding hose pump is a roller pump into which a length of tubing of the tubing system is inserted.

A dialysis fluid pump is provided in the dialysis fluid circulation to transport the dialysis fluid. An ultrafiltration pump generates the required vacuum in the dialysis fluid chamber of the dialyzer, so that fluid which is not replaced by substitute fluid can be withdrawn from the patient to maintain the fluid balance.

An arteriovenous fistula is often created surgically as access to the patient's blood vessel system, this fistula generally being created by puncture using an arterial cannula and a venous cannula. Alternatively, it is possible to use a vascular implant such as a so-called Goretex graft or a so-called PTFE shunt. The term "fistula" is used below to refer to any type of connection between a patient's vein and artery.

The perfusion of a fistula is of great importance for its functionality. If the fistula flow drops below a critical level, the risk of a fistula thrombosis increases along with the risk of losing the vascular access which is essential for the blood purification treatment. Declining fistula flow may be caused by a developing inflow or outflow stenosis in the fistula, calcification of the fistula, filling of the fistula and other similar causes, which are summarized by the term "fistula stenosis" below.

To prevent the negative consequences of a fistula stenosis, it is desirable to discover any developing fistula stenosis as soon as possible or at least before it reaches a critical degree of stenosis.

Various methods have been proposed for this purpose. One group of methods is concerned with measuring the blood flow. DE 19917197 C1 describes a method and a device for determining the blood flow $Q_F$ in a vascular access F during an extracorporeal blood treatment. The determination in the vascular access is based on the fact that the pressure in an arterial and/or venous branch of the extracorporeal circulation is measured with the vascular access both open and interrupted, respectively, during which times the extracorporeal blood flow $Q_B$ changes. Then the fistula flow $Q_F$ is determined from the measured values for the arterial pressure and/or the venous pressure with the vascular access both open and interrupted, respectively.

DE 102008061122 A1 discloses a method for determining and/or monitoring cardio-vascular parameters pertaining to a patient's physical condition and a device for measuring the amplitude of a cardiac pressure signal. The physical state may then be the patency of a fistula.

The object of the present invention is to provide a method which is easy to perform for accurately determining the fistula pressure as well as a device for said purpose. Furthermore, another object of the present invention is to provide a device for predicting an incipient fistula stenosis and a corresponding method.

This object is achieved by a control unit having the features of claim 1. Advantageous embodiments are characterized in dependent claims 2 through 12. A control unit according to the invention for determining the pressure in a blood vessel, which is in fluid connection with at least one section of a blood line system, in particular an extracorporeal blood circulation, is configured to perform the following steps, at least one pressure-generating device suitable for acting on that section being assigned to the blood line system:

a) ensuring that none of the at least one pressure-generating device acts on the section,
b) interrupting the fluid connection of the section with the blood vessel by triggering an interrupt means,
c) setting the pressure in the section at a predetermined ideal value, in particular at ambient pressure, with the help of a pressure sensor in the section,
d) restoring the fluid connection of the section with the blood vessel by triggering the interrupt means, and
e) measuring a pressure thus established in the section with the help of the pressure sensor.

The pressure in the blood vessel may be defined in various ways within the scope of the invention based on a wave-shaped pressure curve in the blood vessel system and thus also when there is a fluid connection in the blood line system. The phrase "pressure in the blood vessel" and the "pressure in the section" are preferably each understood to refer to the average of the wave-shaped pressure curve based on the patient's heartbeat.

In accordance with the use of "mmHg" as the units of pressure for reporting blood pressure in medicine, although typically no longer used otherwise, this being defined as the difference in pressure in a blood vessel with respect to ambient pressure, the pressure is also used as a relative pressure with respect to ambient pressure, expressed in the units "mmHg" within the scope of the invention to report pressure values in the blood line system. A pressure of 0 mmHg in the blood line system thus corresponds to ambient pressure according to this definition.

The pressure in an arteriovenous fistula is preferably determined with the control unit and/or the control unit is configured to determine this pressure. In this case, the pressure in the blood vessel is referred to as the internal fistula pressure or simply the fistula pressure. According to the statements made above, the fistula pressure can be determined by the control unit according to the invention as the average of the maximum fistula pressure and the minimum fistula pressure.

The advantage of the present invention is that the measurement of the pressure is performed in a section of the blood tubing system, which is isolated from interfering influences, starting from a predetermined ideal value. Therefore, error sources that could influence the accuracy of the measured pressure, are ruled out or at least minimized. Error sources that are ruled out and/or minimized may include, for example, the fact that different actual measured pressures are established in each section, starting from different initial pressures levels in different measurements or initial pressures with different plus or minus signs. With such different initial pressures, pressures are also established at different rates. As a result, despite the same final pressures, a measurement after a predetermined period of time may yield different actual measured pressures. Starting from a predetermined pressure, which is advantageously always the same, in the section, the pressure may be determined as the pressure transmitted up to the section in the blood vessel by means of the control unit according to the invention, this pressure being superimposed only on a hydrostatic pressure. In the preferred embodiment, in which the control unit is configured to set the pressure in the section in step c) at ambient pressure, the resulting pressure set in step e) can be determined with a particularly high accuracy.

In the matter of a control step, the step of "being sure" that none of the at least one pressure-generating device is acting on the section includes a first case in which there is already a nonaction which must simply be detected by the control unit and a second case in which the nonaction must also be induced by the control unit.

In the first case, the at least one pressure-generating device, which is suitable for acting on the section, is already not acting on the section. This can be ascertained by the control unit according to the first variant in that the control unit receives a signal from the pressure-generating device indicating that it has already been stopped. The control unit may also be configured to assume a status of nonaction as given when a pressure sensor which is connected to the control unit and is suitable for measuring the pressure in the section supplies the control unit with the information that there is no change in pressure in that section. In addition, the control unit may be configured to assume a status of nonaction of the pressure-generating devices on the section when at least one interrupt means blocks off the section with respect to at least one pressure-generating device.

In the second case, the at least one pressure-generating device also acts on the section. For this case, the control unit may be configured to ascertain this by triggering corresponding means such as, for example, the at least one pressure-generating device, a pressure sensor and/or at least one interrupt means. In this case, the control unit ascertains that the at least one pressure-generating device does not act on the section, that it triggers a means which terminates the action. This triggering means may in turn be the at least one pressure-generating device which also acts on the section and/or at least one interrupt means, which is suitable for blocking off the section from the at least one pressure-generating device. The pressure-generating device may be deactivated, stopped or put into an idling mode, for example, so that it can no longer act on the section. An action of a pressure-generating device on the section is to be understood within the scope of the present invention as referring to any type of pressure change. A shutdown, stoppage or idling operation of the pressure-generating device is an energy-saving measure in particular, preventing great pressure differences from building up in the blood line system, and is gentle for the blood carried in the blood line system. Within the scope of the present invention, the term "stop" or "stoppage" should include all possibilities for shutdown, stoppage and idling operation of a pressure-generating device without having to explain these variants in differentiated terms in each case.

In one variant of the control unit according to the invention, it is configured to trigger at least one of the means mentioned above, which are suitable for terminating an action of at least one pressure-generating device on the section, such as the at least one pressure-generating device or the at least one interrupt means, without first checking on whether there is an action and then to stop the pressure-generating device through this triggering and/or to close the interrupt means.

When it is stated within the context of the invention that the control unit or another suitable unit performs or executes something, this is a simplified notation which should be understood to mean that the control unit or the other suitable unit optionally triggers a suitable actuator or sensor to perform something if the control unit for the other suitable unit is not capable of performing this action itself. Those skilled in the art will know in these cases that the corresponding simplified formulation is to be understood accordingly.

The control unit is advantageously configured to perform steps a) through e) on an arterial section of a blood supply line of the blood line system and/or on a venous section of a blood return line of the blood line system, in particular of an extracorporeal blood circulation. Such sections may be in fluid connection with a blood vessel due to the fact that one end of the arterial and/or venous section is introduced into the blood vessel through an access such as a cannula. If the blood vessel is an arteriovenous fistula, then an arterial cannula can be introduced into an arterial section of the fistula and/or a venous cannula may be introduced into a venous section of the fistula.

The arterial section and/or the venous section of the blood line system is defined as the region of the blood line system facing the blood vessel whose pressure is to be determined. The arterial and venous sections may be joined to one another at their ends facing away from the blood vessel, joining them through the blood chamber of a dialyzer in the case of the presence of an extracorporeal blood circulation, for example, in a hemodialysis machine. An end of the venous and/or arterial section facing away from the blood vessel, whose pressure is determined in step e), may be defined by an interrupt means and/or a blood pump, for example. For example, a peristaltic pump may be introduced as a pressure-generating device into the blood supply line and may define the end of the arterial section facing away from the blood vessel.

The interrupt means triggerable by the control unit in step b) is typically provided on an end of the section facing the blood vessel. It is therefore possible to ensure with little effort that the fluid connection of the blood line system to the blood vessel whose pressure is to be determined can be interrupted.

In addition, the control unit may be configured to trigger at least one additional interrupt means. Thus, for example, the fluid connection between the at least one section and the remaining blood line system, in particular the remaining extracorporeal blood circulation, may be interrupted. This may be advantageous when there are two sections, for example, whose pressures can be measured by the control unit according to the invention in step e). If an ideal pressure value is set in two sections, each independently of the other and at the same time, in step c), for example, and then a resulting pressure is to be measured in step e), it may be advantageous if the two sections are separated from one another by one or more additional interrupt means to ensure that the respective pressures will be established without any mutual influence on the two sections. This may be advantageous in particular if the fluid connection of at least one of the two sections to the remaining blood line system cannot otherwise be established completely or at all.

Interrupt means traditionally used in an extracorporeal blood circulation, for example, hose clamps or valves, can be triggered by the control unit as interrupt means in step a), step b) and step d) and also as further interrupt means.

According to one embodiment, the control unit may be configured to trigger a blood pump as a pressure-generating device, in particular an occlusion pump, such as a peristaltic pump and/or a roller pump. Peristaltic pumps, in particular roller pumps, are traditionally used for transporting blood in blood line systems in medical technology. Peristaltic pumps can be operated by running forward and can be stopped. They may also be suitable for being operated in reverse. The control unit may be figured accordingly. It is also conceivable that the control unit is configured to put the pump in an idling mode, which prevents a pressure from being generated despite the fact that the pump is still running. According to one aspect of the invention, a vacuum in the section is reduced and set at the ideal value, in particular ambient pressure (corresponding to 0 mmHg).

According to another embodiment, the control unit may also be configured so that in step a) and/or step c), at least one further pressure-generating device, in particular a pump, which is assigned to the extracorporeal blood circulation, is to be triggered alternatively or in addition to one blood pump. The additional pump may be a substituate pump which pumps substituate through a substituate fine into the blood supply line (as so-called predilution) and/or into the blood return line (as so-called postdilution).

Alternatively or additionally in step a) and/or step c), the control unit may be configured to trigger a pump as the pressure-generating device in a dialysis fluid circulation that is in fluid connection with the blood line system. This may be an ultrafiltration pump in particular. The ultrafiltration pump traditionally acts on the extracorporeal blood circulation during operation, so that convection toward the dialysis fluid chamber is induced through a semipermeable membrane of a dialyzer which separates a blood chamber from a dialysis fluid chamber. This convection acts as a vacuum on the blood chamber and thus acts on the extracorporeal blood circulation connected to the blood chamber. Generating pressure which can also act on the at least one section is likewise terminated by triggering the ultrafiltration pump and turning off, i.e., stopping it. The principle of the invention is not affected at all by how the respective pumps are situated in the dialysis fluid circulation, in the blood line system and/or in the substituate line system with respect to the line into which they are introduced and with respect to their precise functionality in a blood treatment. Accordingly, the descriptions of the traditional use of the ultrafiltration pump are not to be seen as restrictive but rather only as an example. Thus, for example, the ultrafiltration pump can also induce only that portion of the ultrafiltration that is not compensated by a substitution rate.

According to the invention, it is also conceivable that the control unit is configured to trigger multiple pressure-generating devices, such that the all of these devices together exert a pressure on the at least one section, this pressure being equal to an ideal value, in particular equal to the ambient pressure.

Preferably, however, in step a) all the pressure-generating devices that are capable of acting on the section are triggered by the control unit in such a way that they do not exert any pressure on the section, for example, by stopping them. "Pressure" in the context of the invention is also always used to be an umbrella term for excess pressure and reduced pressure or vacuum, as already explained above, always as the differential pressure with respect to ambient pressure.

According to another variant, the means preventing and/or terminating an action of the pressure-reducing device on the section is an interrupt device such as a clamp or a valve which causes the pressure-generating device to no longer exert a pressure on the section despite the fact that the pressure-generating device continues to run. For example, a venous clamp limits a venous section of the extracorporeal blood circulation to the dialyzer and an ultrafiltration pump acts on the venous section via a dialysis fluid circulation which runs through the dialyzer, so that the action of the ultrafiltration pump is terminated, despite the fact that it continues to run, when the control unit closes the clamp.

The control unit may be configured to perform steps a) through e) in a treatment machine, such as a device for performing hemodialysis, hemofiltration and/or hemodiafiltration. In this preferred variant of the invention, a plurality of actuators (in particular pressure-generating devices and/or interrupt devices) and sensors which can be triggered by the control unit in steps a), b), c), d) and/or e) are existing parts of a blood treatment machine. This has the advantage that the control unit according to the invention can perform at least some of steps a) through e), preferably all of steps a) through e), without requiring any further sensors and/or actuators in addition to the sensors and actuators already present in the blood treatment machine. All actuators and sensors that can be triggered by the control unit in steps a), b), c), d) and/or e) are especially preferably parts of the blood treatment machine.

The control unit may of course also be configured within the scope of the invention to trigger actuators and/or sensors such as pumps, valves, clamps and/or pressure sensors, which do not otherwise have any functions in the blood treatment machine, in one or more of steps a) through e).

According to another preferred variant, the control unit according to the invention may be configured to trigger sensors and actuators in a blood treatment machine within the context of a blood treatment. This has the advantage that one and the same control unit may be used to control the blood treatment machine and to perform a measurement of the pressure in a blood vessel. Accordingly, this reduces the cost, complexity and weight of a combination of the control unit and the blood treatment machine according to the invention.

The control unit may advantageously be configured to perform steps a) through e) at least once during a blood treatment. The statement "during a blood treatment session" according to the present invention comprises any points in time within the scope of a blood treatment session. In a traditional blood treatment session, which is several hours long, this may be at the very beginning of the treatment, at the every end of the treatment or at a point in time between the beginning and the end of the treatment. If steps a) through e) are performed entirely at the beginning of a blood treatment session, then it is advantageous if at least the blood supply line is already filled with the patient's blood whose blood vessel pressure is to be determined. Before step a), the control unit may advantageously monitor whether the blood supply line is filled with blood. This ensures that no air from the blood line system will enter the patient's blood vessel system, especially within the context of step e). However, steps a) through e) according to the invention can also be performed even when the blood line system is filled with air because even when the fluid is air, a fluid connection of the section with the blood vessel may exist and/or may be interrupted and restored.

In addition, it is possible to provide that the control unit is configured to perform steps a) through e) during a plurality of blood treatment sessions. This makes it possible to perform a long-term measurement series to observe the trend in the measured pressure in the section and thus the pressure in the blood vessel such as the fistula pressure.

It may also be advantageous that the control unit is configured to perform steps a) through e) repeatedly during a blood treatment session. This makes it possible to analyze a large number of measured values, which can lead to better precision through averaging, for example.

It is of course also possible to perform steps a) through e) on a patient who is not undergoing a blood treatment at least at the time of the measurement of the pressure in the blood vessel. This may be advantageous, for example, if an even larger number of measurements are to be obtained.

According to one variant of the invention, the control unit is configured to subtract the hydrostatic pressure from the pressure measured in step e). In this way the absolute pressure in the blood vessel is determined without any other pressures being superimposed on it. This has the advantage that even a single measured value can have a high relevance with regard to the condition of the blood vessel. Long-term measurements over multiple blood treatment sessions have less fluctuation in the curve and can lead to more accurate statements about a developing stenosis.

The subtraction may be prompted by the control unit in an evaluation unit, for example. The hydrostatic pressure can be determined and transmitted in various ways. The hydrostatic pressure p(hydr) is calculated using the following equation:

$$p(\text{hydr}) = \rho\, g\, h,$$

where $\rho$=density of blood,
$g$=acceleration due to gravity (9.81 g/ms$^2$),
$h$=difference in height between the pressure sensor and the patient's heart.

According to one aspect, the control unit is configured to inquire about the height difference h via the evaluation unit, for example. An input may be made manually, for example, on an input unit connected to the evaluation unit or may be obtained by measurement. A measurement can be performed by detecting the position of the patient and his heart. It is also possible to use estimated values, approximation values or empirical values, which may be patient-specific, for example. These may in turn be entered manually or inserted by the evaluation unit for the specific patient.

According to another aspect of the invention, the control unit is configured to transmit the pressure in the blood vessel measured in step e) to an evaluation unit, which is configured to analyze a plurality of blood vessel pressure values with regard to a stenosis developing in the blood vessel.

In particular the control unit is configured to transmit a fistula pressure, which is measured in step e), with and/or without a superimposed hydrostatic pressure (i.e., the pressure measured in step e) in that section and/or the calculated pressure in the blood vessel) to an evaluation unit, which is configured to evaluate a plurality of pressure values with regard to a developing stenosis in the blood vessel, in particular a fistula stenosis.

An evaluation of a plurality of blood vessel pressure values, in particular fistula pressure values, may be made on the basis of suitable trend analyses, i.e., long-term testing. Thus the control unit itself or the evaluation unit may be configured to detect a rising pressure in the blood vessel as a sign of a developing stenosis. Instead or in addition, the control unit may be configured to detect a drop in pressure in the blood vessel, an increase or decrease in the first derivation of the pressure as a developing stenosis. Depending on the medical findings about the development of a stenosis and its effects on the pressure in the respective blood vessel, a wide variety of criteria are conceivable for inferring a developing stenosis on the basis of the pressure curve.

In the presence of a predetermined criterion, the control unit or the evaluation unit may deliver a message. This message may be delivered via a signal generator, for example. The control unit and/or evaluation unit may be configured for delivering the message accordingly.

The object of the invention is additionally achieved by a method according to claim 13. With a method according to the invention for determining the pressure in a blood vessel, in particular in an arteriovenous fistula which is in fluid connection with at least one section of a blood line system, in particular of an extracorporeal blood circulation such that at least one pressure-generating device which is suitable for acting on the section is provided, the method comprises the following steps:

a) ensuring that none of the at least one pressure-generating device(s) is acting on the section,
b) interrupting the fluid connection of the section with the blood vessel,
c) setting the pressure in the section at an idea value, in particular at ambient pressure,
d) restoring the fluid connection of the section with the blood vessel and
e) measuring the pressure then established in the section.

Advantageously at least some of the steps are performed with a control unit. This may preferably be the control unit according to the invention. It may be advantageous to perform all the steps with the control unit. However, it may also be advantageous or desirable to perform at least some of the steps manually. To this extent, all the steps and substeps explained above in conjunction with the configuration of the control unit according to the invention should be disclosed as process steps that may be performed by the control unit but may also be performed otherwise, in particular manually, even if this is not stated explicitly below for each individual variant and alternative of steps a) through e). The same thing holds for all the other steps and substeps within the scope of the invention.

The object of the invention is additionally achieved with a blood treatment machine according to claim 15.

A blood treatment machine according to the invention for extracorporeal blood treatment, in particular for hemodialysis, hemofiltration and/or hemodiafiltration is provided for receiving a blood line system of an extracorporeal blood circulation such that the blood line system has an arterial section of a blood supply line and a venous section of a blood return line. The arterial section and/or the venous section are provided for being set in fluid connection with a blood vessel, in particular with an arteriovenous fistula, and the blood treatment machine has at least one pressure-generating device which is suitable for acting on the arterial and/or venous section. In addition, the blood treatment machine has a control unit according to the invention for determining the pressure in the blood vessel.

The invention and additional advantageous variants and embodiments are described in greater detail below on the basis of one exemplary embodiment with reference to the FIGURE.

The FIGURE shows schematically the design of a hemodiafiltration machine (HDF machine) together with a control unit according to the invention for determining the pressure in a blood vessel. The HDF machine can also be interpreted as an HD machine as long as no hemofiltration is being performed and/or as an HF machine as long as no hemodialysis is being performed with it. The blood treatment machine in the exemplary embodiment may therefore also be named accordingly, depending on which type of blood treatment is being discussed. The designations HD, HF and HDF are not to be understood as restrictive.

On the basis of the FIGURE, first the basic design of a hemodiafiltration machine and its connection to the blood vessel system I of a patient (not shown) which is merely indicated here will first be explained in detail briefly. In hemodialysis blood is transported from the blood vessel system I into an extracorporeal blood circulation II. For this purpose, the patient is given a fistula which forms a short circuit between an artery A and a vein V in the lower arm, for example (not shown) and thus creates a so-called arteriovenous fistula. A blood supply line 2 is connected to the fistula F through an arterial cannula 1. Blood from the blood vessel system I is sent through the blood supply line 2 to a blood purification element which is designed as a hemodialyzer 4 by means of a blood pump 3 which is typically designed as an occlusion roller pump. In the hemodialyzer 4, a semipermeable membrane 5 which is preferably designed in the form of a plurality of hollow fibers (not shown) also separates a first chamber 6 which is known as the blood chamber and is part of the extracorporeal blood circulation II from a second chamber 7, which is referred to as the dialysis fluid chamber and is part of a dialysis fluid circulation III. Substances to be removed from the blood pass through the semipermeable membrane 5 into the dialysis fluid and are then removed with the dialysis fluid. At the same time, an excess quantity of fluid can be removed from the blood by ultrafiltration based on a pressure gradient and can also be removed through the outgoing dialysis fluid. The pressure gradient is created by an ultrafiltration pump 8.

The purified blood leaves the blood chamber 6 of the hemodialyzer 4 through a blood return line 9 and is returned to the patient's blood vessel system I via a venous cannula 10 which is used to puncture a portion of the fistula F, which faces the patients vein V. A venous clamp 11 is provided on the blood return line 9 as a venous interrupt means with which the return of blood can be interrupted in emergencies, for example. Such emergencies may occur when air is detected in the blood return line 9 by a blood detector 12 between the dialyzer 4 and the venous clamp 11, for example. An arterial pressure sensor 13 is provided on the blood supply line 2 upstream from the blood pump 3, and a venous pressure sensor 14 is provided on the blood return line 9 upstream from the venous clamp 11.

Dialysis fluid flows through the second chamber 7 of the hemodialyzer 4, said fluid being supplied from a dialysis fluid source 16 via a dialysis fluid supply line 15 and being removed through a dialysis fluid discharge line 17 to an outlet 18. The dialysis fluid is transported by a dialysis fluid pump 19 in the dialysis fluid discharge line 17. Upstream from the dialysis fluid pump 19, an ultrafiltrate line 20, which is connected to the ultrafiltration pump 8 and also leads to the outlet 18 branches off from the dialysis fluid discharge line 17.

To supply fluid to the patient again, the HDF machine has a substitution device 21 with which a substitute fluid (also referred to as substituate) can be supplied to the blood in the extracorporeal blood circulation II. The substitution device 21 has a substituate source 22 for supplying substituate, a first substituate line 23 which is connected to a first substituate pump 24 leading from the substituate source to the blood supply line 2 downstream from the blood pump 3, which is referred to as predilution, because the substituate is supplied upstream from the blood chamber 6. A second substituate line 25 which is connected to a second substituate pump 26 leads from the substituate source 22 to the blood return line 9 downstream from the blood chamber 6 (postdilution). The second substituate line 25 opens into the drip chamber 12 of the return line 9.

Various balancing devices make it possible to coordinate the amount of substituate and dialysis fluid that are supplied and the amount of ultrafiltrate as well as dialysis fluid that are removed in interaction with the aforementioned pumps and possibly additional pumps in a targeted manner. The skilled person has access to a wide variety of embodiments for implementation of a balancing device 27, which balances the supply dialysis fluid and the dialysis fluid removed and possibly additional balancing devices and pumps in the dialysis fluid circulation and in the substitution device, so that detailed explanations are unnecessary at this point. The same thing is also true of providing dialysis fluid through the dialysis fluid source 16 and providing substituate through the substituate source 22.

Numerous possibilities are also available to the skilled person in general in using actuators and sensors in an HDF machine without having to discuss all these possibilities in detail here. The representation in the FIGURE is limited to a few of these actuators and sensors which are sufficient for an explanation of the present invention such as, for example, the venous clamp 11, the arterial pressure sensor 13 and the ultrafiltration pump 8.

The HDF machine is controlled and monitored by a control unit 30. The control unit 30 together with the individual actuators and sensors of the machine is therefore connected to control lines for this purpose. For the actuators and sensors shown in the FIGURE, such as pumps, pressure sensors, clamps and valves, this is indicated only in general terms by a plurality of signal lines 50, which are not shown individually for the individual actuators or sensors because this would otherwise mean a poor comprehensibility, and they are also not labeled with individual reference numerals.

The control unit according to the invention for determining the pressure in a blood vessel is explained in conjunction with the hemodiafiltration machine just described above because most or all of the hardware components triggered according to the invention, in particular the actuators and sensors, are already present in this machine. However, the present invention is not limited to use of the control unit in the specific HDF machine described here. This control unit may be a component of the HDF machine or may be a separate unit which is then to be connected to an existing HDF machine. However, the situation is similar for any other blood treatment machine such as a hemofiltration machine and a hemodialysis machine to which a control unit according to the invention may be connected.

The process steps explained below as being executed by the control unit may additionally be controlled either altogether by the control unit according to the invention or may optionally be executed at least partially manually within the scope of the method according to the invention and/or executed by additional devices such as an evaluation unit, a memory unit, an input unit, a signal generator or other devices, which in turn perform the steps after triggering by the control unit or through manual operation or automatically.

When speaking below of the fact that the control unit or another suitable unit "performs" or "executes" something, for example, measuring a pressure or closing a clamp, this is a shortcut expression which is understood to mean that the control unit or the other suitable unit triggers a suitable actuator or sensor to perform something, optionally after inquiring about a status; for example, it may trigger a pressure sensor to measure a pressure and to report the measured pressure to the control unit or it may trigger a clamp to close, possibly after inquiring as to whether it is already closed, etc. For the sake of simplicity, it is not stipulated here in all cases which actuator or which sensor becomes active after being triggered. The skilled person will know in these cases how the corresponding simplified wording is to be understood.

In the exemplary embodiment of the invention, the control unit 30 is configured to ensure in a step a) that the blood pump is no longer acting on a first section 28 of the blood supply line 2, which extends from the blood pump 3 up to an arterial clamp 29 which can close the blood supply line 2 to the patient and which is also referred to below briefly as the "arterial section." The control unit 30 can therefore trigger the blood pump 3 to stop in step a). Therefore, the generation of a vacuum in the arterial section is terminated. Furthermore, the control unit 30 is configured to interrupt a fluid connection of the arterial section from the arteriovenous fistula by triggering an interrupt means in step b). In this example, it is configured to interrupt the fluid connection of the arteriovenous fistula F by triggering the arterial clamp 29 as the interrupt means and closing it.

The control unit 30 is additionally configured to trigger the blood pump 3 in a step c) as a pressure-generating means, so that an ideal pressure value of 0 mmHg is established in the arterial section 28, i.e., ambient pressure is established. In particular the control unit is configured to allow the blood pump 3 to run forward or in reverse as needed. The control unit 30 is configured so that there is a query of the arterial pressure sensor 13 regarding the pressure in the arterial section 28, and in the event this pressure is positive, to have the blood pump run forward so that a negative pressure is generated upstream from the blood pump 3. The control unit 30 is also configured so that in the event the pressure in the arterial section 28 is negative, the control unit can trigger the blood pump 3 so that it runs in reverse, thereby generating a positive pressure which compensates for the negative pressure up to zero. The "forward" and "reverse" directions of rotation denote the directions which are based on the normal hemodialysis operation described above. To achieve the blood flows in the extracorporeal blood circulation in normal operation from the arterial cannula 1 back to the venous cannula 10 by way of the dialyzer 4 as described with reference to the FIGURE, the blood pump 3 runs "forward" by definition.

The control unit is also configured to restore the fluid connection of the first arterial section 28 with the arteriovenous fistula F in a step d) by opening the arterial clamp 29 after it has been triggered. Furthermore, the control unit is configured to measure a pressure that is established in section 28 by means of the arterial pressure sensor 13 in a step e).

The additional configurations of the control unit are described below within the context of the method according to the invention.

According to the exemplary embodiment of the method according to the invention, the patient is first in an ongoing hemodiafiltration method. This means that the blood pump 3 is pumping blood out of the fistula F through the blood supply line 2 into the first chamber 6 of the hemodialyzer 4 and through the blood return line 9 and the venous channel 10 back into the fistula F. The venous clamp 11 and the arterial clamp 29 in the blood supply line as the arterial interrupt device(s) are opened. Unwanted substances are withdrawn from the blood by the hemodialyzer 4 and the blood is thereby purified. The arterial pressure sensor 13 measures the pressure in the arterial section and the venous pressure sensor 14 measures the pressure in the venous section. These pressures are composed of the dynamic pressure on the arterial and/or venous cannula, the hydrostatic pressure and the fistula pressure. The hydrostatic pressure is formed due to the column of fluid comprised of blood up to the level of the patient's heart which is above the arterial and/or venous pressure sensor in the patient's blood vessels and depends on the position and location of the patient. The fistula pressure also known as the internal fistula pressure, is the pressure in the fistula which ultimately results from the pressure of the heartbeat as the dynamic pressure in the fistula.

Then the blood pump 3 is stopped and both the arterial and venous clamps 29, 11 are closed. The arterial pressure sensor 13 then measures an arterial pressure. Because of the blood pump being stopped, the dynamic pressure drops. The measured pressure therefore has a certain time lag because the dynamic pressure does not drop suddenly after the blood pump is turned off but instead remains running for a few seconds. By closing the clamps 29, 11 the prevailing pressure status is more or less "frozen," i.e., it is uncoupled from the patients blood vessel system I.

Then the pressure in the blood supply line is tared at 0 mmHg, i.e., at ambient pressure. While the arterial clamp 29 remains closed, this is achieved by the fact that a pressure or a vacuum is created with the actuators that are present, this pressure completely compensating from the prevailing in the section whose pressure is being tared. This is achieved in the blood supply line 2 with the blood pump 3.

If there is a negative output pressure in the first arterial section of the blood supply line 2 between the blood pump 3 and the arterial clamp 29 of −180 mmHg, for example, as can typically occur in a blood treatment due to the suction effect upstream from the blood pump 3, then the blood pump 3 is operated in the direction opposite the traditional pump direction in step c), so that a positive pressure is generated. The blood pump 3 is kept running until a pressure of 0 mmHg is established. Then the blood pump 3 is stopped.

If there is instead a positive output pressure in the first arterial section, which is measured by the arterial pressure sensor 13, then the blood pump is operated in its traditional direction in step c). The vacuum created thereby downstream from the blood pump 3 compensates for the positive output pressure accordingly until the value of 0 mmHg, i.e., ambient pressure is achieved. Then the blood pump 3 is stopped.

There is no pressure compensation upstream or downstream of the blood pump due to the fact that the blood pump 3, as a peristaltic pump occludes the tubing in one spot, which forms the section of the blood line system there in the area of the pump. The desired pressure of 0 mmHg can therefore be established accurately in this example because the first arterial section during step c) is a closed system.

Then in a step d) the arterial clamp 29 is opened, so that the fluid connection to the fistula F is restored. A pressure p(art) is established in the arterial section 28 which is measured by the arterial pressure sensor 13. The pressure in the arterial section is composed of the fistula pressure and the hydrostatic pressure. The fistula pressure is the average pressure in the fistula. The patient's heartbeats cause a wave-shaped pressure curve which is attenuated via the blood vessels and the blood line system, in particular due to the constriction of the cannulas 1, 10. It is therefore preferable to use the average pressure in the blood vessel to be measured (fistula here).

If the position of the patients heart is known, then the hydrostatic pressure p(hydr) can be calculated using the equation:

$$P(\text{hydr}) = \rho\, g\, h$$

(where $\rho$=density of the blood, g=acceleration due to gravity, h=height of the heart above the pressure sensor 13) and subtracted from p(art), so that the fistula pressure p(fistula) is obtained as follows:

$$p(\text{fistula}) = p(\text{art}) - p(\text{hydrostat}).$$

This calculation is performed in this exemplary embodiment by an evaluation unit 34. To do so, the medical personnel operating the HDF machine must measure the height of the patient's heart and enter this value into an input unit, namely in this case a touchscreen 33, when the evaluation unit 30 asks for this value. The resulting absolute fistula pressure without a superimposed hydrostatic pressure is reproduced by the evaluation unit, displayed on the screen 33 and stored in the evaluation unit 34.

In the exemplary embodiment, the determination of the fistula pressure described here is performed in each individual blood treatment session with the patient, i.e., typically three times a week. The values of the fistula pressure thereby determined are stored by the evaluation unit with a date notation and plotted in a diagram as a time-dependent measured curve. If the fistula pressure exceeds a predetermined value, a warning is issued and displayed on screen 33, for example. Instead, a warning may also be issued when there is a characteristic curve of the time-dependent measured curve. Depending on where a stenosis develops in or on the fistula, other pressure curves may also be typical. This may occur, for example, when a value is greater than or less than the first derivation over a predetermined value. Predetermined values of the pressure, its derivation or other predetermined curve parameters may be predetermined individually for each patient, for example, as a function of a prevailing hypertension, a preexisting calcification of the blood vessels or some other preexisting illnesses which might influence the fistula pressure and/or its curve over time.

Stenoses in the efferent part of the fistula, so-called outflow stenoses in particular, can be detected easily on the basis of a characteristic increase in fistula pressure by using the method according to the invention.

In one variant of the exemplary embodiment, the control unit 30 is configured to trigger the ultrafiltration pump 8 in step a) and to stop it. In addition, the control unit 30 is configured to also interrupt a section 41 of the blood return line 9 from a fluid connection to the fistula F in step b) between the venous clamp 11 and a clamp 42 arranged downstream from the blood chamber 6, this section also being referred to below briefly as "venous section 41"; this interruption of the section is accomplished by triggering the venous clamp 11 as the interrupt means. Then in step c), the pressure in the venous section, which is originally approx. +200 mmHg in the normal operation, is reduced by the ultrafiltration pump 8 in step c) until the value reaches 0 mmHg, i.e., ambient pressure. Then the ultrafiltration pump is stopped. Again in step d) in the variant, the fluid connection is established by triggering the venous clamp 11. In this variant, the value measured in step e) is the pressure in the venous section 41 measured by the venous pressure sensor 14.

In another variant of the exemplary embodiment, at least one additional pump is provided to perform the taring of at least one of the pressures in the blood supply line and/or in the blood return line. In this variant the control unit 30 is designed to control this at least one additional pump. The at least one additional pump may be an additional pump which already fulfills a different object in hemodialysis than one of the two substituate pumps 24, 26, for example. By pumping substituate into the blood line system 39 the pressure can then be increased. In combination with the ultrafiltration pump in particular, taring of the pressure in the arterial and/or venous sections 28, 41 can be achieved here.

In the case of a blood treatment machine according to the exemplary embodiment, detection of a critical fistula pressure as explained above is performed by the control unit 30.

In the exemplary embodiment, the device according to the invention for performing the method contains a control unit 30, which is designed to perform the computation steps described above for determining the fistula pressure as well as to open and close the clamps 11, 29, 42 as described. In addition, the control unit 30 is designed and provided to trigger the blood pump 3 and the ultrafiltration pump 39 so that the pressures defined can be set.

In another variant of the exemplary embodiment, the hydrostatic pressure is not subtracted from the measured pressure in the arterial and/or venous section. In this case the fistula pressure is determined as the sum together with the hydrostatic pressure. However, long-term trends of an increasing fistula pressure are detected, although the absolute value of the fistula pressure is not calculated, then increases and other trends do not depend on the absolute value of the pressure. In particular when the patient is arranged mostly identically with regard to the position and location in each measurement performed according to the invention during hemodialysis, the hydrostatic pressure has very little influence on the accuracy of the measurement.

The invention is not limited to the exemplary embodiments described here. In particular, any type of pump that is suitable for pumping blood and/or for generating a pressure may be provided in the blood supply line as well as in the blood return line. Furthermore, all the features mentioned above may be combined with one another in any desired way as long as this is reasonable and feasible within the scope of the invention. Individual steps or substeps of the method may all be performed by the control unit or manually at least in part.

The invention claimed is:

1. A control unit (30) for determining the pressure in a blood vessel in fluid connection with at least one section of a blood line system, at least one pressure-generating device assigned to the blood line system being suitable for acting on the section, the control unit being configured to perform the following steps:
   a) being sure that none of the at least one pressure-generating device acts on the section,
   b) interrupting the fluid connection of the section with the blood vessel by triggering an interrupt means,
   c) setting the pressure in the section, while the fluid connection is interrupted, at a predetermined ideal value as measured by a pressure sensor in the section,
   d) restoring the fluid connection of the section with the blood vessel by triggering the interrupt means, and
   e) measuring a resulting pressure in the section by the pressure sensor.

2. The control unit according to claim 1, which is configured to perform steps a) through e) on an arterial section of a blood supply line and/or on a venous section of a blood return line of the blood line system.

3. The control unit according to claim 1, which is configured to perform step a) by triggering the at least one pressure-generating device.

4. The control unit according to claim 1, which is configured to perform step a) as a pressure-generating device by triggering a blood pump.

5. The control unit according to claim 4, which is configured to trigger the blood pump so that it runs in reverse and thereby reduces a vacuum in the section, thereby raising it to the ideal value.

6. The control unit according to claim 5, wherein the ideal pressure value is ambient pressure.

7. The control unit according to claim 4, which is configured to perform step a) and/or c) as the pressure-generating device by triggering an ultrafiltration pump in a dialysis fluid circulation in fluid connection with the blood line system.

8. The control unit according to claim 1, which is configured to perform steps a) through e) in a blood treatment machine.

9. The control unit according to claim 1, which is configured to perform steps a) through e) at least once during a blood treatment session.

10. The control unit according to claim 1, which is configured to perform steps a) through e) during a plurality of blood treatment sessions.

11. The control unit according to claim 1, which is configured to trigger at least one additional interrupt means to interrupt the fluid connection between the at least one section and the remaining blood line system.

12. The control unit according to claim 1, which is configured to trigger an evaluation unit so that the evaluation unit subtracts the hydrostatic pressure from the pressure in the at least one section measured in step e).

13. The control unit according to claim 1, which is configured to transmit the pressure in the blood vessel and/or the pressure in the section, which is measured in step e), to an evaluation unit 34 which is configured to detect a plurality of pressure values indicative of a developing stenosis.

14. A blood treatment machine for extracorporeal blood treatment provided to receive a blood line system of an extracorporeal blood circulation, wherein the blood line system has an arterial section of a blood supply line and/or has a venous section of a blood return line, such that the arterial section and the venous section are provided for being in fluid connection with a blood vessel, the blood treatment machine comprising at least one pressure-generating device suitable for acting on the arterial section and/or the venous section,
   characterized in that
   the blood treatment machine further comprises a control unit for determining the pressure in the blood vessel according to claim 1.

15. The blood treatment machine according to claim 14, wherein the extracorporeal blood treatment is hemodialysis, hemofiltration, or hemodiafiltration, and wherein the blood vessel is an arteriovenous fistula.

16. The control unit according to claim 1, wherein the blood vessel is an arteriovenous fistula, wherein the blood line system is an extracorporeal blood circulation, and wherein the predetermined ideal pressure value is ambient pressure.

17. The control unit according to claim 1, which is configured to perform steps a)-e) in a blood treatment machine selected from the group consisting of a machine for hemodialysis, a machine for hemofiltration, or a machine for hemodiafiltration.

18. A method for determining the pressure in a blood vessel in fluid connection with at least one section of a blood line system cooperating with at least one pressure-generating device suitable for acting on the section, wherein the method comprises the following steps:
   a) being sure that none of the at least one pressure-generating device acts on the section,
   b) interrupting the fluid connection of the section with the blood vessel,
   c) setting the pressure in the section at an ideal value,
   d) restoring the fluid connection of the section with the blood vessel, and
   e) measuring a resulting pressure in the section.

19. The method according to claim 18,
   characterized in that
   at least one of the steps a) through e) is performed by a control unit.

20. The method according to claim 18, wherein the blood vessel is an arteriovenous fistula, the blood line system is an extracorporeal circulation, and the ideal pressure value is ambient pressure.

* * * * *